(12) United States Patent
Taeschler et al.

(10) Patent No.: US 9,809,596 B1
(45) Date of Patent: Nov. 7, 2017

(54) METHOD FOR PREPARATION OF FLUORO, CHLORO AND FLUOROCHLORO ALKYLATED COMPOUNDS BY HOMOGENEOUS CATALYSIS

(71) Applicant: Lonza Ltd, Visp (CH)

(72) Inventors: Christoph Taeschler, Visp (CH); Florencio Zaragoza Doerwald, Visp (CH); Stefan Ellinger, Visp (CH); Matthias Beller, Nienhagen (DE); Helfried Neumann, Rostock (DE); Lin He, Rostock (DE); Kishore Natte, Rostock (DE)

(73) Assignee: Lonza Ltd., Visp (CH)

( * ) Notice: Subject to any disclaimer, the term of this patent is extended or adjusted under 35 U.S.C. 154(b) by 0 days.

(21) Appl. No.: 15/522,336

(22) PCT Filed: Nov. 5, 2015

(86) PCT No.: PCT/EP2015/075763
§ 371 (c)(1),
(2) Date: Apr. 27, 2017

(87) PCT Pub. No.: WO2016/071425
PCT Pub. Date: May 12, 2016

Related U.S. Application Data

(60) Provisional application No. 62/076,618, filed on Nov. 7, 2014.

(30) Foreign Application Priority Data

Nov. 7, 2014 (EP) .................................... 14192280
Aug. 13, 2015 (EP) .................................... 15181003
Aug. 14, 2015 (EP) .................................... 15181019

(51) Int. Cl.
*C07D 473/10* (2006.01)
*C07C 41/30* (2006.01)
*C07C 17/272* (2006.01)
*C07C 45/68* (2006.01)
*C07D 209/10* (2006.01)
*C07D 207/33* (2006.01)
*C07D 333/12* (2006.01)
*C07D 207/333* (2006.01)

(52) U.S. Cl.
CPC .......... *C07D 473/10* (2013.01); *C07C 17/272* (2013.01); *C07C 41/30* (2013.01); *C07C 45/68* (2013.01); *C07D 207/33* (2013.01); *C07D 207/333* (2013.01); *C07D 209/10* (2013.01); *C07D 333/12* (2013.01)

(58) Field of Classification Search
CPC ..................................................... C07D 473/10
See application file for complete search history.

(56) References Cited

PUBLICATIONS

PCT/EP2015/075763 International Search Report and Written Opinion, dated Feb. 9, 2016.
PCT/EP2015/075763 International Preliminary Report on Patentability, dated Sep. 15, 2016.
Rebecca N. Loy et al: "Palladium-Catalyzed C-H Perfluoroalkylation of Arenes", Organic Letters, vol. 13, No. 10, May 20, 2011, pp. 2548-2551.
Theresa Liang et al: Introduction of Fluorine and Fluorine-Containing Functional Groups, Angewandte Chemie International Edition, vol. 52, No. 32, Aug. 5, 2013, pp. 8214-8264.

*Primary Examiner* — Paul V Ward
(74) *Attorney, Agent, or Firm* — Dority & Manning, P.A.

(57) ABSTRACT

The invention discloses a method for preparations of fluoro, chloro and fluorochloro alkylated compounds by homogeneous Pd catalyzed fluoro, chloro and fluorochloro alkylation with fluoro, chloro and fluorochloroalkyl halides in the presence of di(1-adamantyl)-adamantyl-n-butylphosphine and in the presence of 2,2,6,6-tetramethylpiperdine 1-oxyl.

13 Claims, No Drawings

METHOD FOR PREPARATION OF FLUORO, CHLORO AND FLUOROCHLORO ALKYLATED COMPOUNDS BY HOMOGENEOUS CATALYSIS

RELATED APPLICATIONS

This application is the national stage entry of International Patent Application No. PCT/EP2015/075763 having a filing date of Nov. 5, 2015, which claims the filing benefit of U.S. Provisional Application No. 62/076,618, having a filing date of Nov. 7, 2014, European Patent Application No. 14192280.7, having a filing date of Nov. 7, 2014, European Patent Application No. 15181003.3, having a filing date of Aug. 13, 2015, and European Patent Application No. 15181019.9, having a filing date of Aug. 14, 2015, all of which are incorporated herein by reference in their entirety.

FIELD OF THE INVENTION

The invention discloses a method for preparation of fluoro, chloro and fluorochloro alkylated compounds by homogeneous Pd catalyzed fluoro, chloro and fluorochloro alkylation with fluoro, chloro and fluorochloro alkyl halides in the presence of di(1-adamantyl)-n-butylphosphine and in the presence of 2,2,6,6-tetramethylpiperidine 1-oxyl.

BACKGROUND OF THE INVENTION

Organofluorine chemistry plays an important role in medicinal, agricultural, and material sciences and fields. Fluoroalkyl groups have strong effects such as high stability and lipophilicity, in addition, longer fluoroalkyl groups have high water and oil resistance and low friciton.

Loy, R. N., et al., Organic Letters 2011, 13, 2548-2551, discloses Pd-catalyzed coupling of $CF_3$—I with benzene in 26% GC yield.

According to Table 1 entry 10 the coupling of $C_6F_{13}I$ provided 81% yield. But a repetition of this experiment with the bromide instead of the iodide provided less than 1% yield, see Comparative Example 11 herein.

There was a need for homogenous catalyzed method for the preparation of fluoro, chloro and fluorochloro alkylated compounds by direct C—H trifluoromethylation, which provides high yields but does not need the assistance of a directing group or of electron rich aromatic compounds. The method should be applicable to a wide variety of substrates and should be compatible with a wide variety of functional groups. Furthermore the method should not be restricted to iodides as alkylating agents only, but should also work with other halides. And the method should work not only with perfluorinated alkyl iodides, but also with fluorinated, chlorinated and fluorochlorinated alkyl halides, especially for fluorinated alkyl halides.

Unexpectedly the presence of di(1-adamantyl)-n-butylphosphine and 2,2,6,6-tetramethylpiperidine 1-oxyl together with a soluble Pd based catalyst meets these requirements. No dialkylated products are observed.

In this text, the following meanings are used, if not otherwise stated:
Ac acetate;
alkyl linear or branched alkyl;
$BuPAd_2$ CAS 321921-71-5, di(1-adamantyl)-n-butylphosphine;
DMSO dimethylsulfoxide;
eq, equiv equivalent;
halide F—, Cl—, Br— or I—, preferably Cl—, Br—, and I—, more preferably Br— and I—;
halogen F, Cl, Br or I; preferably F, Cl or Br; more preferably F or Cl;
"linear" and "n-" are used synonymously with respect to the respective isomers of alkanes;
MTBE methyl tert-butyl ether;
RT room temperature, it is used synonymously with the expression ambient temperature;
TEA triethylamine;
TEMPO CAS 2564-83-2,2,2,6,6-tetramethylpiperidine 1-oxyl;
TFA trifluoroacetate;
"wt%", "% by weight" and "weight-%" are used synonymously and mean percent by weight.

SUMMARY OF THE INVENTION

Subject of the invention is a method for the preparation of a fluoro, chloro or fluorochloro alkylated compound by a reaction of a compound COMPSUBST with a compound FCLALKYLHALIDE by homogeneous catalysis using a catalyst CAT
in the presence of $BuPAd_2$ and
in the presence of TEMPO and
in the presence of a compound BAS,
BAS is selected from the group consisting of $Cs_2CO_3$, $CsHCO_3$, $NEt_3$, and mixtures thereof;
FCLALKYLHALIDE is a compound of formula (III):

$$R3—X \qquad (III)$$

X is Cl, Br or I;
R3 is $C_{1-20}$ alkyl or a $C_{1-20}$ alkyl, wherein in the alkyl chain at least one of the hydrogens is substituted by F or Cl;
CAT is selected from the group consisting of $Pd(OAc)^2$, $Pd(TFA)_2$, and mixtures thereof;
COMPSUBST is selected from the group consisting of a compound COMPSUBST-I, ethene, cyclohexene, ethine, and polystyrene;
the ethene and the cyclohexene being unsubstituted or substituted by 1, 2 or 3 substitutents selected from the group consisting of $C_{1-10}$ alkyl, $C_{3-8}$ cycloalkyl, $C_{1-4}$ alkoxy, N(R10)R11, CN, NO, $NO_2$, F, Cl, Br, I, $CF_3$, $(CH_2)_m$—C(O)Y1, $S(O)_2R50$, CH═C(H)R28, C≡C—R24, benzyl, phenyl, naphthyl and morpholine;
the ethine being unsubstituted or substituted by 1 substitutent selected from the group consisting of $C_{1-10}$ alkyl, $C_{3-8}$ cycloalkyl, $C_{1-4}$ alkoxy, N(R10)R11, CN, NO, $NO_2$, F, Cl, Br, I, $CF_3$, $(CH_2)_m$—C(O)Y1, $S(O)_2R50$, CH═C(H)R28, C≡C—R24, benzyl, phenyl and naphthyl;
COMPSUBST-I contains a ring RINGA;
RINGA is an unsaturated or aromatic, 5 or 6 membered carbocyclic or heterocyclic ring,
when RINGA is a heterocyclic ring, then RINGA has 1, 2 or 3 identical or different endocyclic heteroatoms independently from each other selected from the group consisting of N, O and S,
when RINGA is a 5 membered ring, then RINGA is unsubstituted or substituted by 1, 2, 3 or 4 identical or different subsitutents,
when RINGA is a 6 membered ring then RINGA is unsubstituted or substituted by 1, 2, 3, 4 or 5 identical or different subsitutents,
any of said subsitutents of RINGA is independently from any other of said substitutent of RINGA selected from the group consisting of $C_{1-10}$ alkyl, $C_{3-8}$ cycloalkyl, C$_{1-4}$ alkoxy, OH, N(R10)R11, CN, NH—OH, NO, NO$_2$, F, Cl, Br, I, CF$_3$, (CH$_2$)$_m$—C(O)Y1, S(O)$_2$R50, CH═C(H)R28, C≡C—R24, benzyl, phenyl and naphthyl;

RINGA can be condensed with a ring RINGB, RINGB is a 5 or 6 membered carbocyclic or heterocyclic ring, when RINGB is a heterocyclic ring, is contains 1, 2 or 3 identical or different endocyclic heteroatoms independently from each other selected from the group consisting of N, O and S;

RINGB is unsubstituted or substituted with 1, 2 or 3 in case of RINGB being a 5 membered ring, with 1, 2, 3 or 4 in case of RINGB being a 6 membered ring, identical or different substitutents independently from each other selected from the group consisting of C$_{1-10}$ alkyl, C$_{3-8}$ cycloalkyl, C$_{1-4}$ alkoxy, OH, N(R17)R18, CN, NH—OH, NO, NO$_2$, F, Cl, Br, I, CF$_3$, (CH$_2$)$_n$—C(O)Y2, S(O)$_2$R51, CH═C(H)R38, C≡C—R34, benzyl, phenyl and naphthyl;

any of said C$_{1-10}$ alkyl substitutent of RINGA or RINGB is unsubstituted or substituted with 1, 2, 3, 4 or 5 identical or different substituents selected from the group consisting of halogen, OH, O—C(O)—C$_{1-5}$ alkyl, O—C$_{1-10}$ alkyl, S—C$_{1-10}$ alkyl, S(O)—C$_{1-10}$ alkyl, S(O$_2$)—C$_{1-10}$ alkyl, O—C$_{1-6}$ alkylen-O—C$_{1-6}$ alkyl, C$_{3-8}$ cycloalkyl and 1,2,4-triazolyl;

any of said benzyl, phenyl and naphthyl substitutent RINGA or RINGB is independently from each other unsubstituted or substituted with 1, 2, 3, 4 or 5 identical or different substituents selected from the group consisting of halogen, C$_{1-4}$ alkoxy, NO$_2$ and CN;

m, n and q are identical or different and independently from each other 0, 1, 2, 3, 4, 5, 6, 7, 8, 9 or 10;

Y1, Y2 and R13 are identical or different and independently from each other selected from the group consisting of H, OH, C(R14)(R15)R16, C$_{1-6}$ alkyl, O—C$_{1-6}$ alkyl, phenyl, benzyl, O-phenyl, O—C$_{1-6}$ alkylen-O—C$_{1-6}$ alkyl and N(R19)R20;

R14, R15 and R16 are identical or different and independently from each other selected from the group consisting of H, F, Cl and Br;

R10, R11, R17, R18, R19 and R20 are identical or different and are independently from each other H or C$_{1-6}$ alkyl, or R10 and R11, R17 and R18 or R19 and R20 represent together a tetramethylene or a pentamethylene chain;

R50 and R51 are identical or different and independently from each other selected from the group consisting of OH, C$_{1-6}$ alkyl and C$_{1-6}$ alkoxy;

R24, R34, R28 and R38 are identical or different and independently from each other selected from the group consisting of H, C$_{1-6}$ alkyl, C(R25)(R26)—O—R27;

R25, R26 and R27 are identical or different and independently from each other selected from the group consisting of H and C$_{1-6}$ alkyl.

DETAILED DESCRIPTION OF THE INVENTION

Preferably, RINGA is a carbocyclic unsaturated ring, a carbocyclic aromatic ring, a heterocyclic unsaturated ring or a heterocyclic aromatic ring.

Preferably, COMPSUBST is selected from the group consisting of compound COMPSUBST-I, ethene, cyclohexene, ethine, and polystyrene;

the ethene and the cyclohexane being unsubstituted or substituted by 1 or 2 substituents selected from the group consisting of C$_{1-10}$ alkyl, C$_{3-6}$ cycloalkyl, C$_{1-4}$ alkoxy, N(R10)R11, CN, F, Cl, Br, I, CF$_3$, (CH$_2$)$_m$—C(O)Y1, S(O)$_2$R50, benzyl, phenyl, naphthyl and morpholine;

the ethine being unsubstituted or substituted by 1 substitutent selected from the group consisting of C$_{1-10}$ alkyl, C$_{3-6}$ cycloalkyl, C$_{1-4}$ alkoxy, N(R10)R11 , CN, F, Cl, Br, I, CF$_3$, (CH$_2$)$_m$—C(O)Y1, S(O)$_2$R50, benzyl, phenyl and naphthyl;

with COMPSUBST-I being selected from the group consisting of

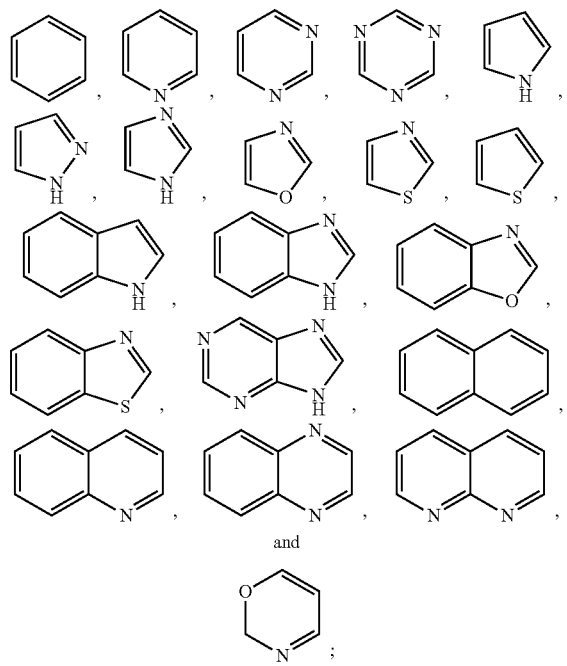

with COMPSUBST-I being unsubstituted or substituted
by 1, 2, 3 or 4 in case of COMPSUBST-I being a monocyclic compound with 5 endocyclic atoms,
by 1, 2, 3, 4 or 5 in case of COMPSUBST-I being a monocyclic compound with 6 endocyclic atoms,
by 1, 2, 3, 4, 5 or 6 in case of COMPSUBST-I being a bicyclic compound wherein a 5-membered and a 6-membered ring are ortho-fused,
by 1, 2, 3, 4, 5, 6 or 7 in case of COMPSUBST-I being a bicyclic compound wherein two 6-membered rings are ortho-fused,
identical or different substituents independently from each other selected from the group consisting of C$_{1-10}$ alkyl, C$_{3-8}$ cycloalkyl, C$_{1-4}$ alkoxy, OH, C(H)═O, N(R10)R11, CN, NH—OH, NO, NO$_2$, F, Cl, Br, I, CF$_3$, (CH$_2$)$_m$—C(O)Y1, S(O)$_2$R50, CH═C(H)R28, C≡C—R24, benzyl, phenyl and naphthyl;

said C$_{1-10}$ alkyl substitutent of COMPSUBST-I is unsubstituted or substituted with 1, 2, 3, 4 or 5 identical or different substituents selected from the group consisting of halogen, OH, O—C(O)—C$_{1-5}$ alkyl, O—C$_{1-10}$ alkyl, S—C$_{1-10}$ alkyl, S(O)—C$_{1-10}$ alkyl, S(O$_2$)—C$_{1-10}$ alkyl, O—C$_{1-6}$ alkylen-O—C$_{1-6}$ alkyl, C$_{3-8}$ cycloalkyl and 1,2,4-triazolyl;

said benzyl, phenyl and naphthyl substitutent of COMPSUBST-I is independently from each other unsubstituted or substituted with 1, 2, 3, 4 or 5 identical or different substituents selected from the group consisting of halogen, C$_{1-4}$ alkoxy, NO$_2$ and CN;

R10, R11, m, n, Y1, Y2, R28, R50 and R24 are defined as above, also with all their embodiments.

Preferably, m, n and q are identical or different and independently from each other 0, 1, 2, 3 or 4:
more preferably, m, n and q are 0 or 4.

In another embodiment, Y1, Y2 and R13 are identical or different and independently from each other selected from the group consisting of H, OH, C(R14)(R15)R16, $C_{2-6}$ alkyl, O—$C_{1-6}$ alkyl, phenyl, benzyl, O-phenyl, O—$C_{1-6}$ alkylen-O—$C_{1-6}$ alkyl and N(R19)R20.

Preferably, Y1, Y2 and R13 are identical or different and independently from each other selected from the group consisting of H, OH, $C_{1-2}$ alkyl, and O—$C_{1-2}$ alkyl.

More preferably, COMPSUBST-I is unsubstituted or substituted
- by 1, 2 or 3 in case of COMPSUBST-I being a monocyclic compound with 5 endocyclic atoms,
- by 1, 2, 3, 4 or 5 in case of COMPSUBST-I being a monocyclic compound with 6 endocyclic atoms,
- by 1, 2, 3, 4 or 5 in case of COMPSUBST-I being a bicyclic compound wherein a 5-membered and a 6-membered ring are ortho-fused,
- by 1, 2, 3 or 4 in case of COMPSUBST-I being a bicyclic compound wherein two 6-membered rings are ortho-fused,
- identical or different substituents independently from each other selected from the group consisting of $C_{1-4}$ alkyl, $C_{1-4}$ alkoxy, OH, C(H)=O, N(R10)R11, CN, F, Cl, Br, $CF_3$, $(CH_2)_m$—C(O)Y1, and $S(O)_2R50$;

said $C_{1-4}$ alkyl substitutent of COMPSUBST-I is substituted or substituted with 1, 2 or 3 identical or different substituents selected from the group consisting of halogen;
with R10, R11, Y1 and R50 as defined above, also with all their embodiments.

Especially, COMPSUBST is selected from the group consisting of benzene, pyrazole,

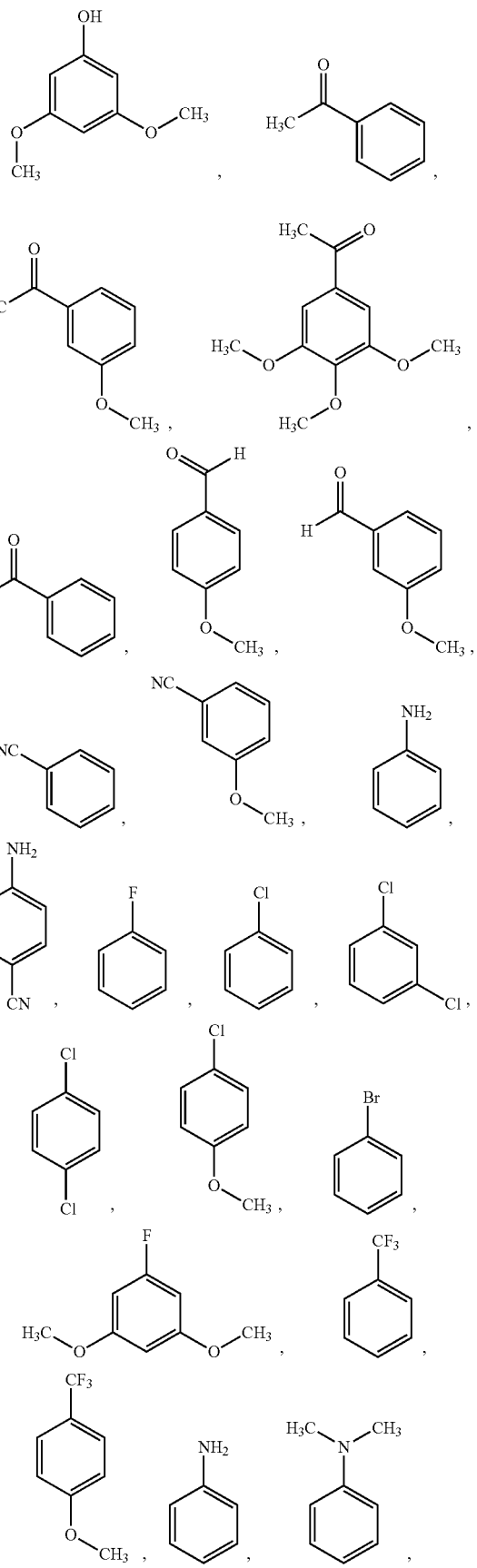

-continued

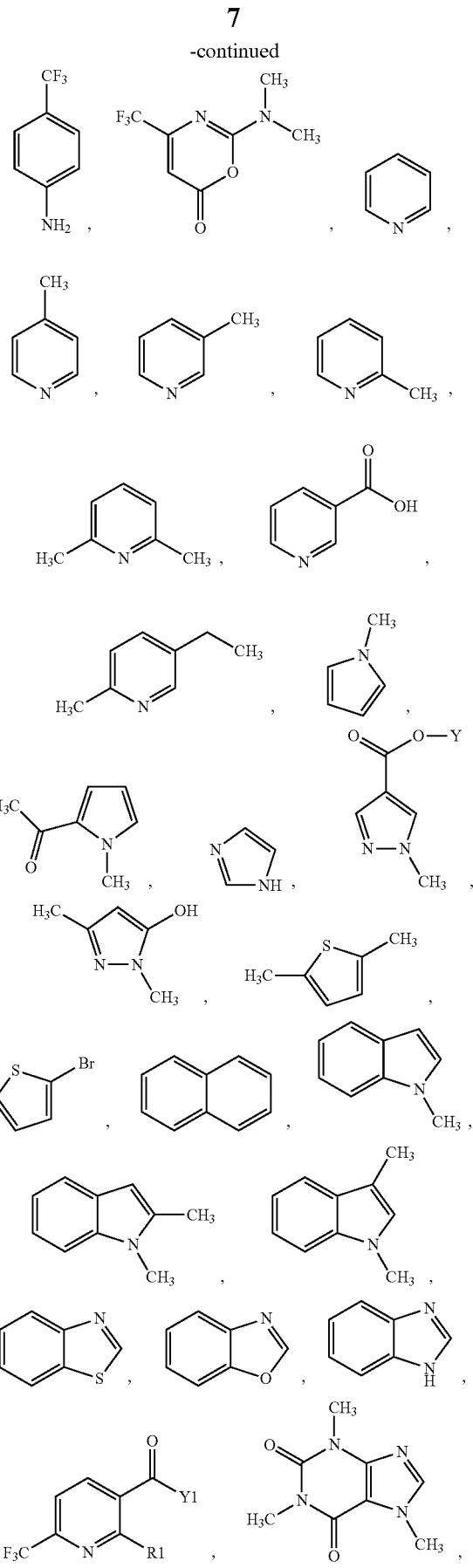

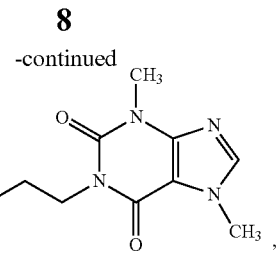

compound of formula (VI), ethene, cyclohexane, ethine, and polystyrene;

Y is $C_{1-6}$ alkyl;

the ethene and the cyclohexene being unsubstituted or substituted by 1 or 2 substitutents selected from the group consisting of $C_{1-10}$ alkyl, $C_{1-4}$ alkoxy, N(R10)R11, CN, F, Cl, Br, I, $CF_3$, $(CH_2)_m$—C(O)Y1, benzyl, phenyl and morpholine;

the ethine being unsubstituted or substituted by 1 substitutent selected from the group consisting of $C_{1-10}$ alkyl, $C_{1-4}$ alkoxy, N(R10)R11, CN, F, Cl, Br, I, $CF_3$, $(CH_2)_m$—C(O)Y1, benzyl and phenyl;

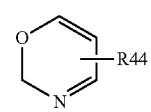

(VI)

wherein

R44 is selected from the group consisting of $C_{1-10}$ alkyl, $C_{1-4}$ alkoxy, OH, N(R10)R11, CN, NO, $NO_2$, F, Cl, Br, I, $CF_3$, $(CH_2)_m$—C(O)Y1, $S(O)_2$R50;

with R10, R11, m, Y1 and R50 as defined above, also with all their embodiments.

Embodiments of the substituted ethene are propene, ethene-1,1-diyldibenzene and 3,3-dimethylbut-1-ene.

An embodiment of substituted cyclohexene is 4-(cyclohex-1-en-1-yl)morpholine.

An embodiment of the substituted ethine is 1-octyne.

Preferably, Y is methyl or ethyl.

An embodiment of COMPSUBST is

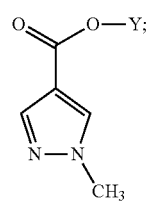

Y is methyl or ethyl, preferably ethyl.

The fluoro, chloro or fluorochloro alkylated compound is called compound ALKYLCOMPSUBST.

The fluoro, chloro and fluorochloro alkyl halide is compound FCLALKYLHALIDE.

Preferably, FCLALKYLHALIDE is a compound of formula (III);

$$R3—X \qquad (III)$$

X is Cl, Br or I;

R3 is $C_{1-20}$ alkyl or a $C_{1-20}$ alkyl, wherein in the alkyl chain at least one of the hydrogens is substituted by F or Cl; more preferably, R3 is $C_{1-15}$ alkyl, wherein in the alkyl chain at least one of the hydrogens is substituted by F or Cl;
even more preferably,
R3 is $C_{1-10}$ alkyl or $C_{1-10}$ alkyl, wherein in the alkyl chain at least one of the hydrogens is substituted by F or Cl.
Preferably,
X is Br or I;
more preferably,
X is I;
in another more preferably embodiment,
X is Br;
also with R3 in all its embodiments.

In an especial ambodiment, compound FCLALKYL-HADLIDE is a perfluoroalkyl halide, $F_2HC$—Cl or $F_2HC$—Br, preferably FCLALKYLHADLIDE is a perfluoroalkylated bromide or iodide, $F_2HC$—Cl or $F_2HC$—Br;
preferably
X is Cl, Br or I, and
R3 is perfluoro $C_{1-20}$ alkyl; or
FCLALKYLHADLIDE is $F_2HC$—Cl or $F_2HC$—Br;
more preferably,
X is Br or I, and
R3 is perfluoro $C_{1-20}$ alkyl; or
FCLALKYLHADLIDE is $F^2HC$—Cl or $F_2HC$—Br;
even more preferably,
X is Br or I, and
R3 is perfluoro $C_{1-15}$ alkyl; or
FCLALKYLHADLIDE is $F_2HC$—Cl or $F_2HC$—Br.

In particular, FCLALKYLHALIDE is selected from the group consisting of $F_{21}C_{10}$—I, $F_{17}C_8$—I, $F_{13}C_6$—I, $F_9C_4$—I, $F_3C$—I, $F_3C$—Br, $F_3C$—Cl, $F_2HC$—Cl, and $F_2HC$—Br;
more in particular, FCLALKYLHALIDE is selected from the group consisting of n-$F_{21}C_{10}$-I, n-$F_{17}C_8$—I, n-$F_{13}C_6$—I, n-$F_9C_4$—I, $F_3C$—I, $F_3C$—Br, $F_3C$—Cl, $F_2HC$—Cl, and $F_2HC$—Br.

In one embodiment, the reaction is done in the presence of a compound COMPSALT;
COMPSALT is selected from the group consisting of NaI, KI, CsI and N(R30)(R31)(R32)R33I;
R30, R31, R32 and R33 are identical or different and independently from each other selected from the group consisting of H and $C_{1-10}$ alkyl;
preferably, R30, R31, R32 and R33 are identical or different and independently from each other selected from the group consisting of H and $C_{2-6}$ alkyl;
more preferably, COMPSALT is selected from the group consisting of NaI and (n-Bu)$_4$NI.

The reaction is preferably done in the presence of a compound COMPSALT and X is Cl or Br, preferably X is Cl.

Preferably, CAT is Pd(OAc)$_2$.
Preferably, from 0.1 to 20 mol%, more preferably from 1 to 15 mol%, even more preferably from 2.5 to 12.5 mol%, of CAT are used in the reaction, the mol% are based on the molar amount of COMPSUBST.
Preferably, from 1 to 20 mol equivalents, more preferably 1 to 15 mol equivalents, even more preferably from 1 to 10 mol equivalents, of FCLALKYLHALIDE are used in the reaction, the mol equivalents are based on the molar amount of COMPSUBST.

In case of FCLALKYLHALIDE being in gaseous form, preferably FCLALKYLHALIDE was used in the reaction in an amount which corresponds to a pressure of from 1 to 10 bar, more preferably from 1 to 5 bar, at ambient temperature.

Preferably, from 1 to 40 mol%, more preferably 5 to 30 mol%, even more preferably from 5 to 25%, of BuPAd$_2$ are used in the reaction, the mol% are based on the molar amount of COMPSUBST.
Preferably, from 0.1 to 10 mol equivalents, more preferably 0.5 to 5 mol equivalents, even more preferably from 0.75 to 2.5 mol equivalents, of TEMPO are used in the reaction, the mol equivalents are based on the molar amount of COMPSUBST.
Preferably, BAS is Cs$_2$CO$_3$.
Preferably, from 0.1 to 10 mol equivalents, more preferably 0.5 to 5 mol equivalents, even more preferably from 0.75 to 2.5 mol equivalents, of BAS are used in the reaction, the mol equivalents are based on the molar amount of COMPSUBST.

The reaction temperature of the reaction is preferably from 20 to 200° C., more preferably from 50 to 200° C., even more preferably from 50 to 150° C., especially from 100 to 150° C., more especially from 110 to 145° C.

The reaction time of the reaction is preferably from 1 h to 60 h, more preferably from 10 h to 50 h, even more preferably from 15 h to 50 h.

Preferably, the reaction is done under inert atmosphere. Preferably, the inert atmosphere is achieved by the use if an inert gas preferably selected from the group consisting of argon, another noble gas, lower boiling alkane, nitrogen and mixtures thereof.

The lower boiling alkane is preferably a $C_{1-3}$ alkane, i.e. methane, ethane or propane.

The reaction can be done in a closed system, it can be done at a pressure caused by the chosen temperature in a closed system, and/or caused by the pressure applied by COMPSUBST, in case that COMPSUBST is in gaseous form. It is also possible to apply pressure with said inert gas. It is also possible to carry out the reaction at ambient pressure.

The reaction can be done in a solvent SOL, SOL is preferably selected from the group consisting of alkanes, chlorinated alkanes, ketones, ethers, esters, aliphatic nitrils, aliphatic amides, sulfoxides, and mixtures thereof;
preferably SOL is selected from the group consisting of $C_{5-8}$ alkane, chlorinated $C_{5-8}$ alkane, acetone, methylethylketone, diethylketone, MTBE, tetrahydrofuran, methyltetrahydrofuran, ethylacetate, butylacetate, valeronitril, acetonitrile, dimethylformamide, dimethylacetamide, N-methylpyrrolidone, dimethylsulfoxide, and mixtures thereof;
more preferably SOL is selected from the group consisting of acetone, methylethylketone, diethylketone, valeronitril, acetonitrile, dimethylsulfoxide, and mixtures thereof;
even more preferably SOL is selected from the group consisting of acetone, methylethylketone, diethylketone, dimethylsulfoxide, and mixtures thereof.

It is also possible to use COMPSUBST simultaneously as substrate and as solvent.

As an alternative, the reaction can also be carried out in the absence of a solvent. In another embodiment, COMPSUBST is used as SOL.

The amount of SOL is preferably from 0.1 to 100 fold, more preferably from 1 to 50 fold, even more preferably from 1 to 25 fold, of the weight of COMPSUBST.

After the reaction, ALKYLCOMPSUBST can be isolated by standard methods such as evaporation of volatile components, extraction, washing, drying, concentration, crystallization, chromatography and any combination thereof, which are known per se to the person skilled in the art.

COMPSUBST, BAS, CAT, BuPAd₂, TEMPO and FCLA-LKYLHALIDE, the fluoro, chloro and fluorochloro alkyl halide, are commercially available and can be prepared according to known precedures.

EXAMPLES

Yield

The yield is given in % as a molar yield of the expected ALKYLCOMPSUBST in the reaction mixture after the reaction, and is based on molar amount of COMPSUBST and was determined by $^{19}F$ NMR with 1,4 difluorobenzene as internal standard, if not otherwise stated.

Isolated yield was derived from the weight of the isolated product and is based on the weight of COMPSUBST, isolated yield is given in parenthesis in Table 1.

Ratio of Isomers and Position of Alkylation were determined by NMR spectroscopy

Example 1

An oven-dried 4 mL vial with stir bar was charged with Pd(OAc)₂ (10 mol%), BuPAd₂ (20 mol%), TEMPO (1.0 eq), Cs₂CO₃ (2.0 eq), 1, 4 dimethoxybenzene (0.2 mmol, 1 eq). Then, acetone (0.5 mL) were injected into the vial under argon flow, The vial was placed in an alloy plate, which was transferred into a 300 mL autoclave of the 4560 series from Parr Instruments under an argon atmosphere. A pressure of 3 to 5 bar CF₃Br followed by 15 bar of N₂ was adjusted at ambient temperature. The reaction mixture was stirred at 130° C. for 40 h. After the reaction was finished, the autoclave was cooled down to room temperature and the pressure was released.

The reaction mixture was extracted with water and ethyl acetate (5 times, each time with 3 mL). The organic layers were washed with brine, dried over Na₂SO₄, and evaporated to yield the crude product. The yield was 81 %.

The purification was done by flash chromatography on silica gel (eluent: heptanes:EtOAc=60:40 (v/v)). Isolated yield was 69%.

Details are also given in Table 1

Example 2

Example 1 repeated with the sole difference that Pd(TFA)₂ was used as CAT instead of Pd(OAc)₂. The yield was 78%.

Example 3

Example 1 repeated with the diffenerence that only 5 mol% of Pd(OAc)₂ were used instead of 10 mol%, and that only 10 mol% BuPAd₂ were used instead of 20 mol%. The yield was 42%.

Example 4

Example 1 repeated with the sole diffenerence that the reaction mixture was stirred at 130° C. for 30 h instead of 40 h. The yield was 70%.

Examples 5 to 21

Example 1 was repeated with the difference that as COMPSUBST the compound listed in Table 1 was used.

TABLE 1

| Example | COMPSUBT | ALYKLCOMPSUBST | Yield (Ratio of Isomers) |
|---|---|---|---|
| 1 | 1,4-dimethoxybenzene | 2-(trifluoromethyl)-1,4-dimethoxybenzene | (69) |
| 5 | 1,3,5-trimethoxybenzene | 2-(trifluoromethyl)-1,3,5-trimethoxybenzene | (81) |
| 6 | 1,3-dimethoxybenzene | (trifluoromethyl)-1,3-dimethoxybenzene (a,b) | (76) (2:1 of a:b) |

TABLE 1-continued

| Example | COMPSUBT | ALYKLCOMPSUBST | Yield (Ratio of Isomers) |
|---------|----------|----------------|--------------------------|
| 7 | 1,2-dimethoxybenzene | 4-(trifluoromethyl)-1,2-dimethoxybenzene | (52) |
| 8 | naphthalene | 1-(trifluoromethyl)naphthalene | 78 (3:1 of a:b) |
| 9 | benzene | (trifluoromethyl)benzene | 72 |
| 10 | 1,4-dimethylbenzene | 2-(trifluoromethyl)-1,4-dimethylbenzene | 61 |
| 11 | 1,2,3,4-tetramethylbenzene | 5-(trifluoromethyl)-1,2,3,4-tetramethylbenzene | 25 |
| 12 | 1,3,5-trimethylbenzene (mesitylene) | 2-(trifluoromethyl)-1,3,5-trimethylbenzene | 53 |
| 13 | methoxybenzene (anisole) | (trifluoromethyl)methoxybenzene | 70 (2:1.2:1 of a:b:c) |
| 14 | 3,4,5-trimethoxyacetophenone | 2-(trifluoromethyl)-3,4,5-trimethoxyacetophenone | (47) |

TABLE 1-continued

| Example | COMPSUBT | ALYKLCOMPSUBST | Yield (Ratio of Isomers) |
|---|---|---|---|
| 15 | 1,3-dimethylindole | 1,3-dimethyl-2-(trifluoromethyl)indole | (79) |
| 16 | 1,2-dimethylindole | 1,2-dimethyl-3-(trifluoromethyl)indole | (76) |
| 17 | 1-methylpyrrole | 1-methyl-2-(trifluoromethyl)pyrrole | 80 |
| 18 | 2-acetyl-1-methylpyrrole | 2-acetyl-1-methyl-5-(trifluoromethyl)pyrrole | (64) |
| 19 | 2,5-dimethylthiophene | 2,5-dimethyl-3-(trifluoromethyl)thiophene | (79) |
| 20 | caffeine | 8-(trifluoromethyl)caffeine | (61) |
| 21 | pentoxifylline | 8-(trifluoromethyl)pentoxifylline | (48) |

Example 22

An oven-dried 4 mL with stir bar was charged with Pd(OAc)$_2$ (10 mol%), BuPAd$_2$ (20 mol%), TEMPO (1.0 eq), Cs$_2$CO$_3$ (2.0 eq), benzene (0.6 mmol, 1 eq) and perfluorohexyl bromide (3.2 eq). Then, acetone (2.5 mL) were injected into the vial under argon flow. The vial was placed in an alloy plate, which was transferred into a 300 mL autoclave of the 4560 series from Parr Instruments under an argon atmosphere. A pressure of 15 bar of N$_2$ was adjusted at ambient temperature. The reaction mixture was stirred at 130° C. for 40 h. After the reaction was finished, the autoclave was cooled down to room temperature and the pressure was released.

The reaction mixture was extracted with water and ethyl acetate (5 times, each time with 3 mL). The organic layers were washed with brine, dried over Na$_2$SO$_4$, and evaporated to yield the crude product. The reaction mixture was analyzed by $^{19}$F-NMR by which an yield of 21% (perfluorohexyl)benzene was found. The identity of the (perfluorohexyl)benzene was confirmed by GC-MS.

A repetition of the experiment provided 28% yield with a conversion of 35%.

Example 23

An oven-dried 4 mL vial with stir bar was charged with Pd(OAc)$_2$ (10%), BuPAd$_2$ (20 mol%), TEMPO (1.0 eq), CsCO$_3$ (2.0 eq), 1,4-dimethoxybenzene (0.2 mmol, 1 eq) and perfluorohexyl bromide (3.2 eq). Then, acetone (1 mL) were injected into the vial under argon flow. The vial was placed in an alloy plate, which was transferred into a 300 mL autoclave of the 4560 series from Parr Instruments under an argon atmosphere. A pressure of 15 bar of N$_2$ was adjusted at ambient temperature. The reaction mixture was stirred at 130° C. for 40 h.

After the reaction was finished, the autoclave was cooled down to room temperature and the pressure was released.

The reaction mixture was extracted with water and ethyl acetate (5 times, each time with 3 mL). The organic layers were washed with brine, dried over Na$_2$SO$_4$, and evaporated to yield the crude product. The reaction mixture was analyzed by GC—MS by which an yield of 42% 1,4-dimethoxy-2-(perfluorohexy)benzene was found.

Example 24

An oven-dried 4 mL vial with stir bar was charged with Pd(OAc)$_2$ (10 mol%), BuPAd$_2$ (20 mol%), TEMPO (1.0 eq), Cs$_2$CO$_3$ (2.0 eq), ethene-1,1-diyldibenzene (0.5 mmol, 1 eq) Then, acetone (2 mL) were injected into the vial under argon flow. The vial was placed in an alloy plate, which was transferred into a 300 mL autoclave of the 4560 series from Parr Instruments under an argon atmosphere. A pressure of 3 to 5 bar CF$_3$Br followed by 15 bar of N$_2$ was adjusted at ambient temperature. The reaction mixture was stirred at 130° C. for 40 h. After the reaction was finished, the autoclave was cooled down to room temperature and the pressure was released.

The reaction mixture was filtered and the filter residue was washed with ethylacetate and acetone. The combined filtrates were concentrated on a rotary evaporator. The residue was purified by column chromatography on silica gel (eluent: heptanes:EtOAc=90:10 (v/v)). Isolated yield was 58%.

$^1$H NMR Analysis of the obtained product showed a 2:1 mixture of (3,3,3-trifluoroprop-1-ene-1,1-diyl) dibenzene and (3,3,3-trifluoropropane-1,1-diyl)dibenzene. The identities of (3,3,3-trifluoroprop-1-ene-1,1-diyl)dibenzene and (3,3,3-trifluoropropane-1,1-diyl)dibenzene were confirmed by GC-MS.

Examples (Ex) 25 and 26 and Comparative Examples (CompEx) 1 to 10

Standard Procedure:

An oven-dried 4 mL vial with stir bar was charged with Pd(OAc)$_2$ (10 mol%), BuPAd$_2$ (20 mol%), ADDITIVE (1.0 eq), BASE (2.0 eq) and 1,4 dimethoxybenzene (0.2 mmol, 1 eq). Then, SOLVENT (0.5 mL) was injected into the vial under argon flow. The vial was placed in an alloy plate, which was transferred into a 300 mL autoclave of the 4560 series from Parr Instruments under an argon atmosphere. A pressure of 3 to 5 bar CF$_3$Br followed by 15 bar of N$_2$ was adjusted at ambient temperature. The reaction mixture was stirred at 130° C. for 40 h.

After the reaction was finished, the autoclave was cooled down to room temperature and the pressure was released.

The reaction mixture was extracted with water and ethyl acetate (5 times, each time with 3 mL). The organic layers were washed with brine, dried over Na$_2$SO$_4$, and evaporated to yield the crude product. The yield of the product was determined by $^{19}$F-NMR spectroscopy.

In CompEx 4 Pd(TFA)$_2$ was used as CAT instead of Pd(OAc)$_2$.

Table 2 shows the parameters that were tested.

TABLE 2

| | ADDITIVE | BASE | SOLVENT | YIELD ($^{19}$F-NMR) |
|---|---|---|---|---|
| CompEx 1 | 1,4-Benzoquinone | Cs$_2$CO$_3$ | Acetone | 38% |
| CompEx 2 | Pivalic acid | Cs$_2$CO$_3$ | Acetone | 31% |
| CompEx 3 | Ag$_2$O | Cs$_2$CO$_3$ | Acetone | 23% |
| CompEx 4 | TEMPO | K$_2$CO$_3$ | Acetone | 35% |
| CompEx 5 | TEMPO | Na$_2$CO$_3$ | Acetone | 42% |
| Ex 25 | TEMPO | TEA | Acetone | 51% |
| CompEx 6 | TEMPO | CsI | Acetone | 14% |
| CompEx 7 | TEMPO | CsF | Acetone | 26% |
| CompEx 8 | TEMPO | NaI | Acetone | 19% |
| CompEx 9 | TEMPO | K$_3$PO$_4$ | Acetone | 4% |
| CompEx 10 | TEMPO | K-tert. butoxide | Acetone | 39% |
| Ex 26 | TEMPO | Cs$_2$CO$_3$ | DMSO | 74% |

Example 27

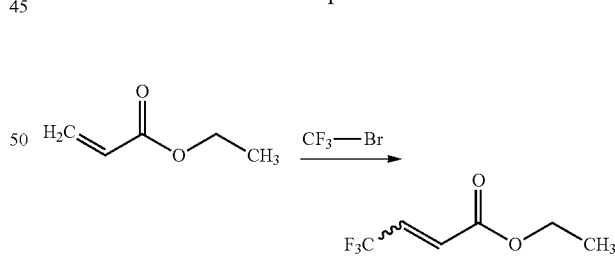

An oven-dried 4 mL vial with stir bar was charged with Pd(OAc)$_2$ (10 mol%), BuPAd$_2$ (20 mol%), TEMPO (1 eq), Cs$_2$CO$_3$ (2.0 eq) and ethyl acrylate (0.5 mmol, 1 eq). Then, acetone (0.5 mL) were injected into the vial under argon flow sequentially. The vial was placed in an alloy plate, which was transferred into a 300 mL autoclave of the 4560 series from Parr Instruments under an argon atmosphere. A pressure of 3 to 5 bar CF$_3$Br followed by 15 bar of N$_2$ was adjusted at ambient temperature. The reaction mixture was stirred at 130° C. for 40 h.

After the reaction was finished, the autoclave was cooled down to room temperature and the pressure was released.

The resulting reaction mixture was cooled, the pressure released from the autoclave, and the solids filtered. The filtered reaction mixture was analyzed by $^{19}$F-NMR using the internal standard 1,4-difluorobenzene showing an yield of 26% of ethyl-4,4,4-trifluorobut-2-enoat (delta $^{19}$F-NMR: −65.68 ppm (d, J=9.5 Hz)). GC-MS Analysis showed a molecular weight peak at 168 g/mol confirming monotrifluormethylation.

Comparative Example 11

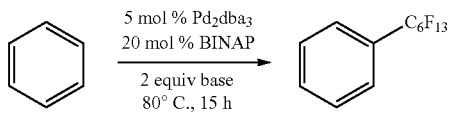

The entry 10 in Table 1 of Loy, R. N., et al., Organic Letters 2011, 13, 2548-2551, was repeated according to the detailed procedure given in the Supporting Information for said article, which is described under "Optimization procedure" on page S3 in connection with entry 9 in Table S4 on page S5.

The phosphine was BINAP.
[Pd] was Pd$_2$dba3.
The base was Cs$_2$CO$_3$.
The alkylhalogenid was perfluorohexyl bromide instead of perfluorohexyl iodide.

To a screw cap 1 dram vial was added base (0.4 mmol, 2 equiv), [Pd] (0.02 mmol, 10 mol%) and phosphine (0.04-0.08 mmol, 20-40 mol%). Benzene (1 mL) and perfluorohexyl bromide (43 microL, 0.2 mmol, 1 equiv) were added, and the resulting mixture was sealed with a Teflon-lined cap and heated in an aluminum reaction block with a vigorous stirring for 15 h at 80° C. The reaction mixture was cooled to 23° C. and chlorobenzene (20 microL) was added as a GC internal standard. An aliquot (~100 microL) was removed from the crude reaction mixture and passed through a plug of Celite, eluting with EtOAc (2 mL). This sample was then analyzed by GC, and the yield was determined by comparison to a calibration against the chlorobenzene internal standard.

Result

A yield of less than 1% was measured.

Example 28

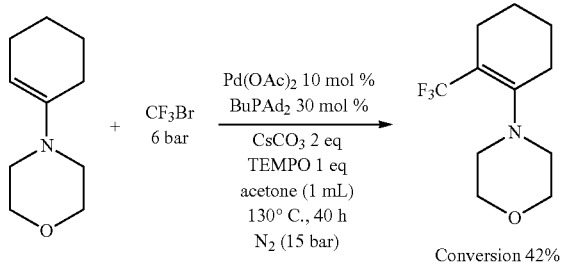

A dried 50 mL autoclave was charged with 4-(cyclohex-1-en-1-yl)morpholine (0.2 mmol), Pd(OAc)$_2$ (10 mol%), BuPAd$_2$ (20 mol%), TEMPO (1.0), Cs$_2$CO$_3$ (2.0 equivalents). Then, acetone (2 mL) was injected into the autoclave and the autoclave was flushed with argon for 3 times. A pressure of 6 bar CF$_3$Br followed by 15 bar of N$_2$ was adjusted at ambient temperature. The reaction mixture was heated at 130° C. for 40 h. The autoclave was placed in a heating system and heated at 130° C. for 40 h. After the completion of the reaction, the autoclave was cooled down to room temperature and the pressure was released. 20 micdoL of 1,2 difluorobenzene (internal standard) was added to the reaction mixture and a sample was submitted for $^{19}$F NMR. The yield was measured by $^{19}$F NMR. The NMR data is in accordance with the literature N. V. Kirij et al., Journal of Fluorine Chemistry, 2000, 106, 217 to 221.

The invention claimed is:

1. A method for the preparation of a fluoro, chloro or fluorochloro alkylated compound by a reaction of a compound COMPSUBST with a compound FCLALKYLHALIDE by homogeneous catalysis using a catalyst CAT
in the presence of BuPAd$_2$ and
in the presence of TEMPO and
in the presence of a compound BAS,
BAS is selected from the group consisting of Cs$_2$CO$_3$, CsHCO$_3$, NEt$_3$, and mixtures thereof;
FCLALKYLHALIDE is a compound of formula (III);

$$R3-X \qquad (III)$$

X is Cl, Br or I;
R3 is C$_{1-20}$ alkyl or a C$_{1-20}$ alkyl, wherein in the alkyl chain at least one of the hydrogens is substituted by F or Cl;
CAT is selected from the group consisting of Pd(OAc)$_2$, Pd(TFA)$_2$, and mixtures thereof;
COMPSUBST is selected from the group consisting of a compound COMPSUBST-I, ethene, cyclohexene, ethine, and polystyrene;
the ethene and the cyclohexene being unsubstituted or substituted by 1, 2 or 3 substituents selected from the group consisting of C$_{1-10}$ alkyl, C$_{3-8}$ cycloalkyl, C$_{1-4}$ alkoxy, N(R10)R11, CN, NO, NO$_2$, F, Cl, Br, I, CF$_3$, (CH$_2$)$_m$—C(O)Y1, S(O)$_2$R50, CH═C(H)R28, C═C—R24, benzyl, phenyl, naphthyl and morpholine;
the ethine being unsubstituted or substituted by 1 substituent selected from the group consisting of C$_{1-10}$ alkyl, C$_{3-8}$ cycloalkyl, C$_{1-4}$ alkoxy, N(R10) R11, CN, NO, NO$_2$, F, Cl, Br, I, CF$_3$, (CH$_2$)$_m$—C (O)Y1, S(O)$_2$R50, CH═C(H)R28, C═C—R24, benzyl, phenyl and naphthyl;
COMPSUBST-1 contains a ring RINGA;
RINGA is an unsaturated or aromatic, 5 or 6 membered carbocyclic or heterocyclic ring,
when RINGA is a heterocyclic ring, then RINGA has 1, 2 or 3 identical or different endocyclic heteroatoms independently from each other selected from the group consisting of N, O and S,
when RINGA is a 5 membered ring, then RINGA is unsubstituted or substituted by 1, 2, 3 or 4 identical or different substituents,
when RINGA is a 6 membered ring then RINGA is unsubstituted or substituted by 1, 2, 3, 4 or 5 identical or different substituents,
any of said substituents of RINGA is independently from any other of said substituent of RINGA selected from the group consisting of C$_{1-10}$ alkyl, C$_{3-8}$ cycloalkyl, C$_{1-4}$ alkoxy, OH, N(R10)R11, CN, NH—OH, NO, NO$_2$, F, Cl, Br, I, CF$_3$, (CH$_2$)$_m$—C(O)Y1, S(O)$_2$R50, CH=C(H)R28, C≡C—R24, benzyl, phenyl and naphthyl;

RINGA can be condensed with a ring RINGB, RINGB is a 5 or 6 membered carbocyclic or heterocyclic ring, when RINGB is a heterocyclic ring, is contains 1, 2 or 3 identical or different endocyclic heteroatoms independently from each other selected from the group consisting of N, O and S;

RINGB is unsubstituted or substituted with 1, 2 or 3 in case of RINGB being a 5 membered ring, with 1, 2, 3 or 4 in case of RINGB being a 6 membered ring, identical or different substituents independently from each other selected from the group consisting of C$_{1-10}$ alkyl, C$_{3-8}$ cycloalkyl, C$_{1-4}$ alkoxy, OH, N(R17)R18, CN, NH—OH, NO, NO$_2$, F, Cl, Br, I, CF$_3$, (CH$_2$)$_n$—C(O)Y2, S(O)$_2$R51, CH=C(H)R38, C≡C-R34 benzyl, phenyl and naphthyl;

any of said C$_{1-10}$ alkyl substituent of RINGA or RINGB is unsubstituted or substituted with 1, 2, 3, 4 or 5 identical or different substituents selected from the group consisting of halogen, OH, O—C(O)—C$_{1-5}$ alkyl, O—C$_{1-10}$ alkyl, S—C$_{1-10}$ alkyl, S(O)—C$_{1-10}$ alkyl, S(O$_2$)-C$_{1-10}$ alkyl, O—C$_{1-6}$ alkylen-O—C$_{1-6}$ alkyl, C$_{3-8}$ cycloalkyl and 1,2,4-triazolyl;

any of said benzyl, phenyl and naphthyl substituent of RINGA or RINGB is independently from each other unsubstituted or substituted with 1, 2, 3, 4 or 5 identical or different substituents selected from the group consisting of halogen, C$_{1-4}$ alkoxy, NO$_2$ and CN;

m, n and q are identical or different and independently from each other 0, 1, 2, 3, 4, 5, 6, 7, 8, 9 or 10;

Y1, Y2 and R13 are identical or different and independently from each other selected from the group consisting of H, OH, C(R14)(R15)R16, C$_{1-6}$ alkyl, O—C$_{1-6}$ alkyl, phenyl, benzyl, O-phenyl, O—C$_{1-6}$ alkylen-O—C$_{1-6}$ alkyl and N(R19)R20;

R14, R15 and R16 are identical or different and independently from each other selected from the group consisting of H, F, Cl and Br;

R10, R11, R17, R18, R19 and R20 are identical or different and are independently from each other H or C$_{1-6}$ alkyl, or R10 and R11, R17 and R18 or R19 and R20 represent together a tetramethylene or a pentamethylene chain;

R50 and R51 are identical or different and independently from each other selected from the group consisting of OH, C$_{1-6}$ alkyl and C$_{1-6}$ alkoxy;

R24, R34, R28 and R38 are identical or different and independently from each other selected from the group consisting of H, C$_{1-10}$ alkyl, C(R25)(R26)—O—R27;

R25, R26 and R27 are identical or different and independently from each other selected from the group consisting of H and C$_{1-10}$ alkyl.

2. The method according to claim 1, wherein

COMPSUBST is selected from the group consisting of compound COMPSUBST-I, ethene, cyclohexene, ethine, and polystyrene;

the ethene and the cyclohexene being unsubstituted or substituted by 1 or 2 substituents selected from the group consisting of C$_{1-10}$ alkyl, C$_{3-6}$ cycloalkyl, C$_{1-4}$ alkoxy, N(R10)R11, CN, F, Cl, Br, I, CF$_3$, (CH$_2$)$_m$—C(O)Y1, S(O)$_2$R50, CH=C(H)R28, C≡C—R24, benzyl, phenyl, naphthyl and morpholine;

the ethine being unsubstituted or substituted by 1 substituent selected from the group consisting of C$_{1-10}$ alkyl, C$_{3-6}$ cycloalkyl, C$_{1-4}$ alkoxy, N(R10)R11, CN, F, Cl, Br, I, CF$_3$, (CH$_2$)$_m$—C(O)Y1, S(O)$_2$R50, benzyl, phenyl and naphthyl;

with COMPSUBST-I being selected from the group consisting of

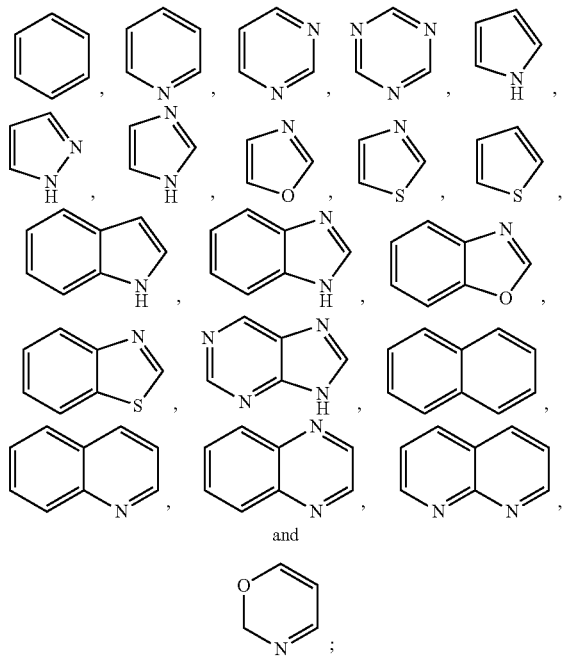

and with COMPSUBST-I being unsubstituted or substituted
by 1, 2, 3 or 4 in case of COMPSUBST-I being a monocyclic compound with 5 endocyclic atoms,
by 1, 2, 3, 4 or 5 in case of COMPSUBST-I being a monocyclic compound with 6 endocyclic atoms,
by 1, 2, 3, 4, 5 or 6 in case of COMPSUBST-I being a bicyclic compound wherein a 5-membered and a 6-membered ring are ortho-fused,
by 1, 2, 3, 4, 5, 6 or 7 in case of COMPSUBST-I being a bicyclic compound wherein two 6-membered rings are ortho-fused,
identical or different substituents independently from each other selected from the group consisting of C$_{1-10}$ alkyl, C$_{3-8}$ cycloalkyl, C$_{1-4}$ alkoxy, OH, C(H)=O, N(R10)R11, CN, NH—OH, NO, NO$_2$, F, Cl, Br, I, CF$_3$, (CH$_2$)$_m$—C(O)Y1, S(O)$_2$R50, CH=C(H)R28, C≡C—R24, benzyl, phenyl and naphthyl;

said C$_{1-10}$ alkyl substituent of COMPSUBST-I is unsubstituted or substituted with 1, 2, 3, 4 or 5 identical or different substituents selected from the group consisting of halogen, OH, O—C(O)—C$_{1-5}$ alkyl, O—C$_{1-10}$ alkyl, S—C$_{1-10}$ alkyl, S(O)—C$_{1-10}$ alkyl, S(O$_2$)—C$_{1-10}$ alkyl, O—C$_{1-6}$ alkylen-O—C$_{1-6}$ alkyl, C$_{3-8}$ cycloalkyl and 1,2,4-triazolyl;

said benzyl, phenyl and naphthyl substituent of COMPSUBST-I is independently from each other unsubstituted or substituted with 1, 2, 3, 4 or 5 identical or different substituents selected from the group consisting of halogen, C$_{1-4}$ alkoxy, NO$_2$ and CN.

3. The method according to claim 1, wherein m, n and q are identical or different and independently from each other 0, 1, 2, 3 or 4.

4. The method according to claim 1, wherein COMPSUBST is selected from the group consisting of benzene, pyrazole,
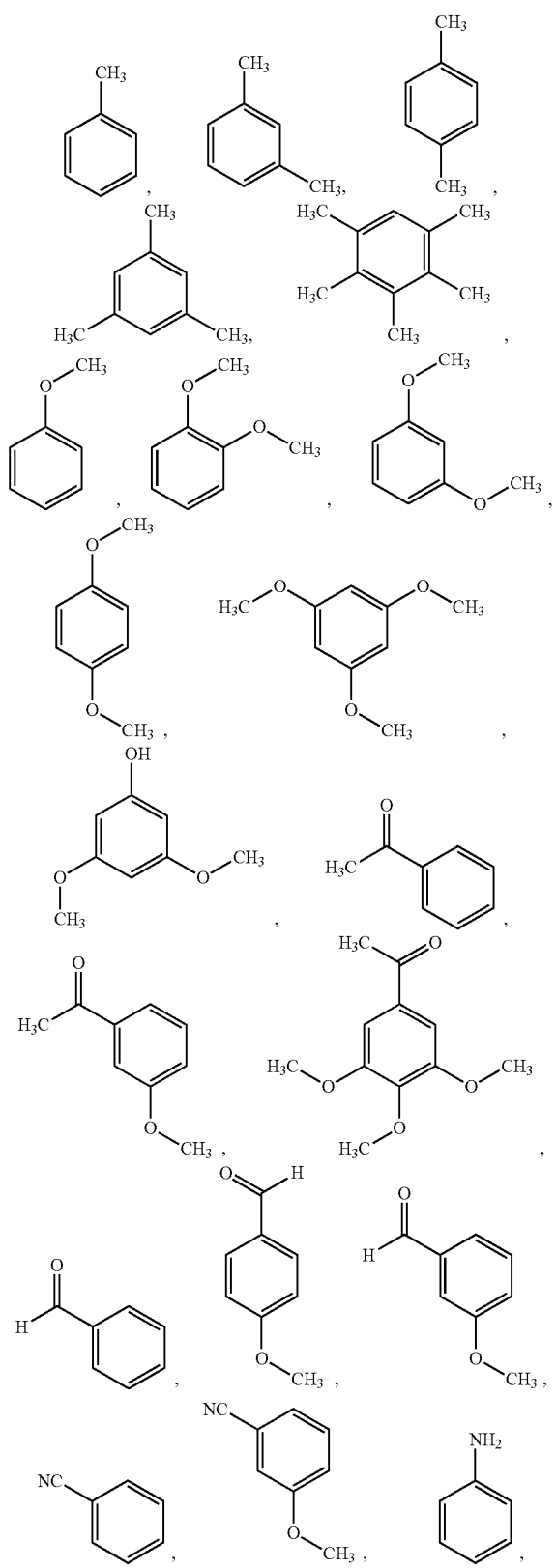
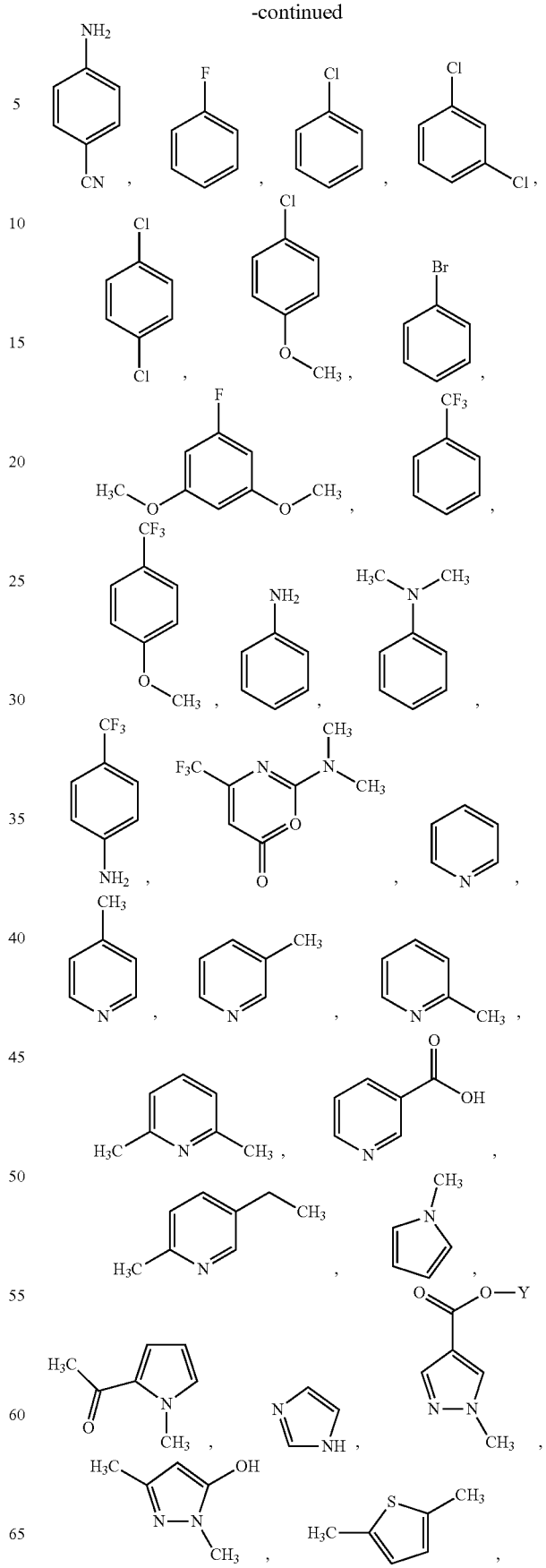

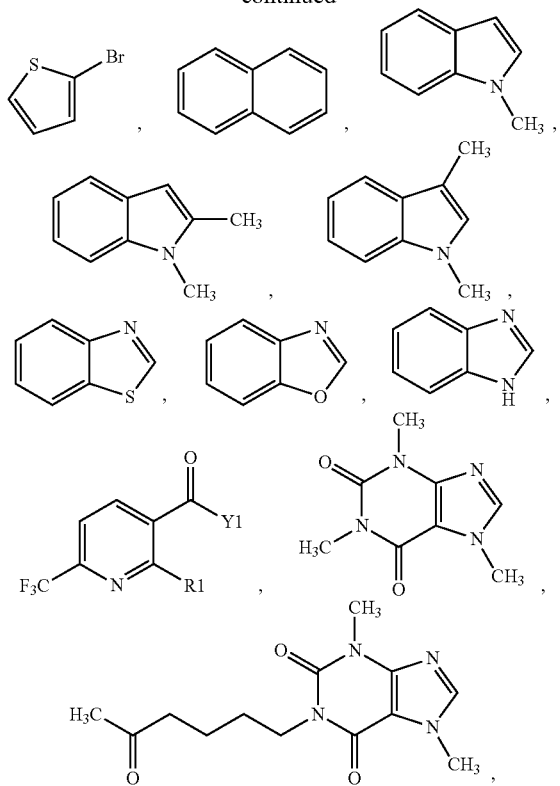

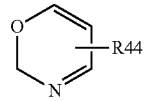

wherein
R44 is selected from the group consisting of $C_{1-10}$ alkyl, $C_{1-4}$ alkoxy, OH, N(R10)R11, CN, NO, $NO_2$, F, Cl, Br, I, $CF_3$, $(CH_2)_m$—C(O)Y1, $S(O)_2R50$.

5. The method according to claim 1, wherein X is Br or I.

6. The method according to claim 1, wherein X is Br.

7. The method according to claim 1, wherein compound FCLALKYLHADLIDE is a perfluoroalkyl halide, $F_2HC$—Cl or $F_2HC$—Br.

8. The method according to claim 1, wherein
X is Cl, Br or I, and
R3 is perfluoro $C_{1-20}$ alkyl, or
FCLALKYLHADLIDE is $F_2HC$—Cl or $F_2HC$—Br.

9. The method according to claim 1, wherein FCLALKYLHALIDE is selected from the group consisting of $F_{21}C_{10}$—I, $F_{17}C_8$—I, $F_{13}C_6$—I, $F_9C_4$—I, $F_3C$—I, $F_3C$—Br, $F_3C$—Cl, $F_2HC$—Cl, and $F_2HC$—Br.

10. The method according to claim 1, wherein
the reaction is done in the presence of a compound COMPSALT;
COMPSALT is selected from the group consisting of NaI, KI, CsI and N(R30)(R31)(R32)R33I;
R30, R31, R32 and R33 are identical or different and independently from each other selected from the group consisting of H and $C_{1-10}$ alkyl.

11. The method according to claim 10, wherein R30, R31, R32 and R33 are identical or different and independently from each other selected from the group consisting of H and $C_{2-6}$ alkyl.

12. The method according to claim 10, wherein COMPSALT is selected from the group consisting of NaI and $(n-Bu)_4NI$.

13. The method according to claim 1, wherein CAT is $Pd(OAc)_2$.

\* \* \* \* \* compound of formula (VI), ethene, cyclohexene, ethine, and polystyrene;
Y is $C_{1-6}$ alkyl;
the ethene and the cyclohexene being unsubstituted or substituted by 1 or 2 substituents selected from the group consisting of $C_{1-10}$ alkyl, $C_{1-4}$ alkoxy, N(R10)R11, CN, F, Cl, Br, I, $CF_3$, $(CH_2)_m$—C(O)Y1, benzyl, phenyl and morpholine;
the ethine being unsubstituted or substituted by 1 substituent selected from the group consisting of $C_{1-10}$ alkyl, $C_{1-4}$ alkoxy, N(R10)R11, CN, F, Cl, Br, I, $CF_3$, $(CH_2)_m$—C(O)Y1, benzyl and phenyl;